United States Patent
Narayan et al.

(10) Patent No.: US 9,914,733 B2
(45) Date of Patent: Mar. 13, 2018

(54) BIISOQUINOLINE COMPOUNDS AND METHODS OF TREATMENT

(71) Applicant: UNIVERSITY OF FLORIDA RESEARCH FOUNDATION, Gainesville, FL (US)

(72) Inventors: Satya Narayan, Gainesville, FL (US); Sukwon Hong, Gainesville, FL (US); Aruna S. Jaiswal, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 15/301,445

(22) PCT Filed: Mar. 30, 2015

(86) PCT No.: PCT/US2015/023439
§ 371 (c)(1),
(2) Date: Oct. 3, 2016

(87) PCT Pub. No.: WO2015/153518
PCT Pub. Date: Oct. 8, 2015

(65) Prior Publication Data
US 2017/0183349 A1    Jun. 29, 2017

Related U.S. Application Data

(60) Provisional application No. 61/975,604, filed on Apr. 4, 2014.

(51) Int. Cl.
*C07D 471/16* (2006.01)
*A61K 31/4745* (2006.01)
*C07D 471/14* (2006.01)

(52) U.S. Cl.
CPC .................. *C07D 471/14* (2013.01)

(58) Field of Classification Search
CPC ........................ C07D 471/16; A61K 31/4745

USPC ............................................ 546/52; 514/283
See application file for complete search history.

(56) References Cited

PUBLICATIONS

International Search Report and Written Opinion dated Jul. 9, 2015 in connection with Application No. PCT/US2015/023439.
Henry et al., Intramolecular cyclization of N-alkyl-3,3',4,4'-tetrahydro-1,1'-biisoquinolinium salts, J. Org. Chem., Jun. 1972;37(12):2039-40. doi: 10.1021/jo00977a040.
Jaiswal et al., Anti-tumor activity of novel biisoquinoline derivatives against breast cancers, Bioorg Med Chem Lett. Oct. 15, 2014;24(20):4850-3. doi: 10.1016/j.bmcl.2014.08.053. Epub Sep. 2, 2014.
Maiti et al., Polymorphic nucleic Acid binding of bioactive isoquinoline alkaloids and their role in cancer, J Nucleic Acids. 2010;2010. pii:593408. doi: 10.4061/2010/593408. Epub Dec. 15, 2009.
Narayan et al., Novel biisoquinoimidazolium-derivatives for breast cancer therapy. Poster presented at the American Association of Cancer Research (AACR) Conference. San Diego, CA. Apr. 7, 2014. 1 page.
Seo et al., Development of biisoquinoline-based chiral diaminocarbene ligands: enantioselective SN2' allylic alkylation catalyzed by copper-carbene complexes. J Org Chem. Mar. 7, 2008;73(5):1983-6. doi: 10.1021/jo702512z. Epub Feb. 12, 2008.
Takagi et al., Synthesis of green and blue fluorescent ladder-type conjugated imidazolium compounds, Org Biomol Chem. Apr. 14, 2013;11(14):2245-8. doi: 10.1039/c3ob40164b.
Zhang et al., Novel Bioactive Isoquinoline Alkaloids from Carduus crispus, Tetrahedron. Aug. 2002;58(34):6795-98. doi: 10.1016/S0040-4020(02)00792-5.

*Primary Examiner* — Charanjit Aulakh
(74) *Attorney, Agent, or Firm* — Wolf, Greenfield & Sacks, P.C.

(57) ABSTRACT

The instant invention describes biisoquinoline compounds having therapeutic activity, and methods of treating disorders such as cancer, tumors and cell proliferation related disorders, or affect cell differentiation, dedifferentiation or transdifferentiation.

19 Claims, No Drawings

BIISOQUINOLINE COMPOUNDS AND METHODS OF TREATMENT

CROSS REFERENCE TO RELATED APPLICATIONS

This application is the U.S. National Stage, pursuant to 35 U.S.C. § 371, of International Application No. PCT/US2015/023439 filed Mar. 30, 2015, which claims the benefit of U.S. Provisional Patent Application Ser. No. 61/975,604, filed Apr. 4, 2014, the contents of which are expressly incorporated by reference herein.

STATEMENT OF RIGHTS TO INVENTIONS MADE UNDER FEDERALLY SPONSORED RESEARCH

This work invention was made with government support under Grant No. CA100247 awarded by the National Institutes of Health, and by the Florida Department of Health, Grant No. 08KN-04. The government has certain rights in the invention.

BACKGROUND

Breast cancers exhibit genetic alterations representing an accumulation of mutations, failure of DNA repair, activation of oncogenes, and loss of tumor suppressor function [Osborne, C.; Wilson, P.; Tripathy, D. Oncologist 2004, 9, 361; Benson, J. R.; Liau, S. S. Surg. Clin. N. Am. 2008, 88, 681]. These genetic defects result in inappropriate intracellular signaling pathways that lead to the initiation, progression, and invasion of breast tumorigenesis [Visbal, A. P.; Lewis, M. T. Curr. Drug Targets. 2010, 11, 1103]. Breast cancer development may be associated with the presence or absence of estrogen receptor (ER), progesterone receptor (PR), and human epidermal growth factor-2 receptor (HER2) [Goldhirsch, A.; Ingle, J. N.; Gelber, R. D.; Coates, A. S.; Thürlimann, B.; Senn, H. J. Ann. Oncol. 2009, 20, 1319]. A positive receptor status is associated with favorable prognostic features and predicts response to hormonal therapy; however, this is balanced by a higher recurrence rate in subsequent years [Ellis, M. J. J. Natl. Cancer Inst. 2008, 100, 159; Abramson, V.; Arteaga, C. L. Clin. Cancer Res. 2011, 17, 952]. ER-, PR- and HER2-negative (triple-negative) breast cancers, which are poorly differentiated and generally fall into the basal subgroup of breast cancers, are significantly more aggressive [Rakha, E. A.; Tan, D. S.; Foulkes, W. D.; Ellis, I. O.; Tutt, A.; Nielsen, T. D.; Reis-Filho, J. S. Breast Cancer Res. 2007, 9, 404; Pal, S. K.; Childs, B. H.; Pegram, M. Breast Cancer Res. Treat. 2011, 125, 627]. Due to the absence of specific treatment guidelines for triple-negative breast cancers, they are managed with standard treatments; however, such treatments are associated with a high rate of local and systemic relapse [Cleator, S.; Heller, W.; Coombes, R. C. Lancet Oncol. 2007, 8, 235; Stockmans, G.; Deraedt, K.; Wildiers, H.; Moerman, P.; Paridaens, R. Curr. Opin. Oncol. 2008, 20, 614; Arslan, C.; Dizdar, O.; Altundag, K. Expert. Opin. Pharmacother. 2009, 10, 2081; Carey, L.; Winer, E.; Viale, G.; Cameron, D.; Gianni, L. Nat. Rev. Clin. Oncol. 2010, 7, 683].

ER, a transcription factor involved in the development and maintenance of female reproductive organs, drives the tumor growth in ~70% of all cases [Greene, G. L.; Gilna, P.; Waterfield, M.; Baker, A.; Hort, Y.; Shine, J. Science 1986, 231, 1150]. Most chemotherapeutic anticancer drugs used in the clinical setup include anti-estrogenic agents that interfere with ER and prevent tumor progression [Nicholson, R. I.; Johnston, S. R. Breast Cancer Res. Treat. 2005, 93, S3; Regierer, A. C.; Wolters, R.; Kurzeder, C.; Wockel, A.; Novopashenny, I.; Possinger, K.; Wischnewsky, M. B.; Kreienberg, R. Breast Cancer Res. Treat. 2011, 128, 273]. Mitosis and other distinct pathways of apoptosis are considered as a potential target for the development of novel class of drugs that can overcome the limitations of current tubulin-targeted antimitotic drugs [Wood, K. W.; Cornwell, W. D.; Jackson, J. R. Curr Opin Pharmacol. 2001, 1,370]. Usually, normal cells avoid mitotic catastrophe by activating different cell cycle checkpoints, which allows them to repair the damage prior to entering mitosis. In contrast, cancer cells are mostly deficient in some of the cell cycle checkpoints [Shapiro, G. I.; Harper, J. W. J. Clin. Invest. 1999, 104, 1645; Blajeski, A. L.; Phan, V. A.; Kottke, T. J.; Kaufmann, S. H. J. Clin. Invest. 2002, 110, 91; Deng, C. X. Nucleic Acids Res. 2006, 34, 1416; Abraham, R. T. Genes Dev. 2001, 15, 2177]. This deficiency in the cell cycle checkpoint is important, as it increases chances for cancer cells to enter mitosis before repairing the damage. The accumulation of unrepaired DNA damage triggers mitotic catastrophe to these cells. It is believed that the treatment-induced growth inhibition by anticancer drugs is due to apoptosis, senescence and/or mitotic catastrophe [de Bruin, E. C.; Medema, J. P. Cancer Treat. Rev. 2008, 34, 737; Okada, H.; Mak, T. W. Nat. Rev. Cancer 2004, 4, 592; Vakifahmetoglu, H.; Olsson, M.; Zhivotovsky, B. Cell Death. Differ. 2008, 15, 1153].

Despite the increased understanding of the molecular events involved in the initiation and progression of breast cancer, and the influence of microenvironment on cancer cell growth, the therapeutic outcome of drugs is still far from the maximum efficiency. Currently, few treatment options for the intervention and prevention of early breast cancer (docetaxel, pacilitexal and trastuzumab) and for the advanced or metastatic breast cancer (gemcitabine, lapatinab and bevacizumab) are available [Takeda, A.; Loveman, E.; Harris, P.; Hartwell, D.; Welch, K. Health Technol Assess 2008, 12, 1]. Most of these drugs act by inducing tubulin polymerization, forming multi-polar spindles, causing DNA damage, and leading to mitotic arrest [Bollag, D. M.; McQueney, P. A.; Zhu, J.; Hensens, O.; Koupal, L.; Liesch, J.; Goetz, M.; Lazarides, E.; Woods, C. M.; Cancer Res. 1995, 55, 2325]. Since the success with existing drugs is still awaited, the new class of anti-estrogen drugs for breast cancer treatment are continuously generated and tested for longer survival with recurrence of the disease. Anti-cancer drugs, which induce DNA damage become resistant, and their therapeutic outcome becomes limited [Chuthapisith, S.; Eremin, J. M.; El-Sheemy, M.; Eremin, O. Surgeon 2006, 4, 211; Gonzalez-Angulo, A. M.; Morales-Vasquez, F.; Hortobagyi, G. N. Adv. Exp. Med. Biol. 2007, 608, 1]. Thus, there is clearly an urgent need for the development of new therapeutic treatment strategies.

Polymethoxylated phenyl rings are often found in the structure of anti-cancer agents such as steganacin [Kupchan, M. S.; Britton, R. W.; Ziegler, M. F.; Gilmore, C. J.; Restivo, R. J.; Bryan, R. F. J. Am. Chem. Soc. 1973, 95, 1335; Tomioka, K.; Ishiguro, T.; Mizuguchi, H.; Komeshima, N.; Koga, K.; Tsukagoshi, S.; Tsuruo, T.; Tashiro, T.; Tanida, S.; Kishi, T. J. Med. Chem. 1991, 34, 54], colchicines [Pohle, K.; Matthies, E.; Peters, J. E. Arch. Geschwulstforsch. 1965, 25, 17; Chen, J.; Liu, T.; Dong, X.; Hu, Y. Mini-Rev. Med. Chem. 2009, 9, 1174], podophyllotoxin [Gordaliza, M.; Castro, M. A.; Corral, J. M. M.; San Feliciano, A. Curr Pharm Des 2000, 6, 1811; You Y, J. Curr. Pharm. Des. 2005, 11, 1695], and noscapine [Ye, K.; Ke, Y.; Keshava, N.; Shanks, J.; Kapp, J. A.; Tekmal, R. R.; Petros, J.; Joshi, H. C. *Proc. Natl. Acad. Sci. USA.* 1998, 95, 1601].

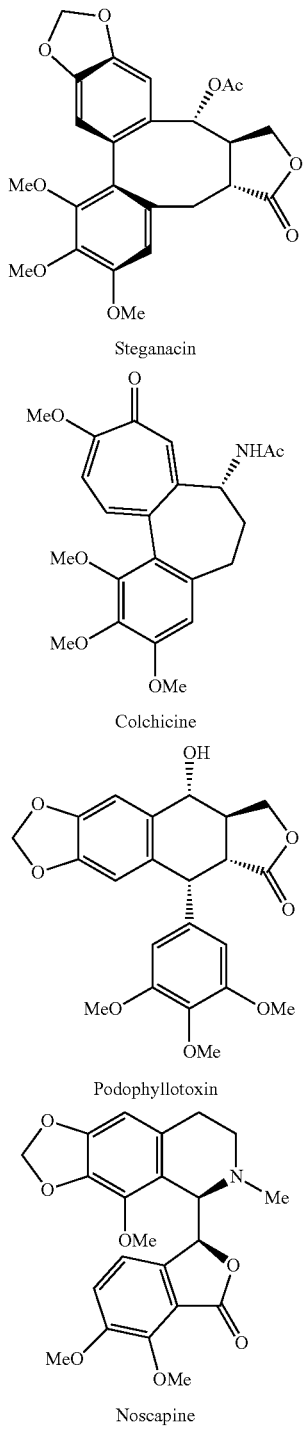

Presented herein are methoxylated biisoquinoline compounds, which can be conveniently prepared in three steps from commercial starting materials, rendering their lead optimization process facile compared to structurally more complex natural products. Herein, we report syntheses of variously methoxylated biisoquinoline derivatives and their highly potent growth inhibitory effects on both triple-positive and triple-negative human breast cancer cell lines.

BRIEF SUMMARY OF THE INVENTION

The invention is directed towards biisoquinoline-containing compounds, and methods of treating disease and disorders, including proliferation diseases and disorders, by use of the compounds and compositions thereof.

The invention is directed towards biisoquinoline-containing compounds, methods of modulating proliferation activity, and methods of treating proliferation disease and disorders.

In one embodiment, the invention provides a compound according to Formula I:

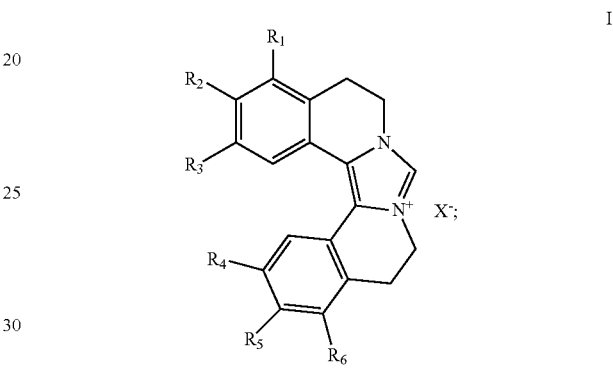

wherein:
$R_1$, $R_2$, $R_3$, $R_4$, $R_5$, and $R_6$ are each independently H or alkoxy;
$X^-$ is halide, $^-OC(O)$—$R_7$, $^-OSO_2$—$R_7$, or $^-OR_7$; and
each $R_7$ is independently H, optionally substituted alkyl, optionally substituted aryl, optionally substituted arylalkyl, haloalkyl, optionally substituted cycloalkyl, optionally substituted heterocycloalkyl, or optionally substituted heteroaryl;
and pharmaceutically acceptable salts, solvates, or hydrates thereof.

In one embodiment, the invention provides a compound according to Formula I:

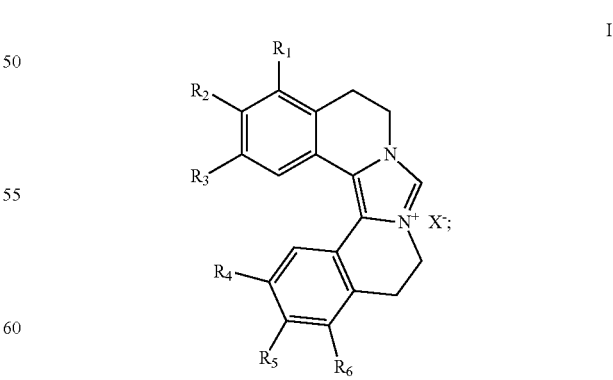

wherein:
$R_1$, $R_2$, $R_3$, $R_4$, $R_5$, and $R_6$ are each independently H or alkoxy;
$X^-$ is halide, $^-OC(O)$—$R_7$, $^-OSO_2$—$R_7$, or $^-OR_7$; and each $R_7$ is independently H, optionally substituted alkyl, optionally substituted aryl, optionally substituted arylalkyl, haloalkyl, optionally substituted cycloalkyl, optionally substituted heterocycloalkyl, or optionally substituted heteroaryl;

provided that when $R_2$ and $R_5$ are methoxy, then at least one of $R_1$, $R_3$, $R_4$, and $R_6$ is alkoxy;

and pharmaceutically acceptable salts, solvates, or hydrates thereof.

In another aspect, the invention provides a compound according to Formula I:

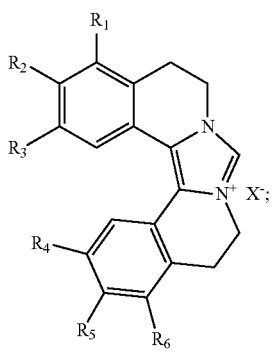

I wherein:

$R_1$, $R_2$, $R_3$, $R_4$, $R_5$, and $R_6$ are each independently H or alkoxy, wherein at least one of $R_1$, $R_3$, $R_4$, and $R_6$ is alkoxy;

$X^-$ is halide, $^-OC(O)$—$R_7$, $^-OSO_2$—$R_7$, or $^-OR_7$; and each $R_7$ is independently H, optionally substituted alkyl, optionally substituted aryl, optionally substituted arylalkyl, haloalkyl, optionally substituted cycloalkyl, optionally substituted heterocycloalkyl, or optionally substituted heteroaryl;

and pharmaceutically acceptable salts, solvates, or hydrates thereof.

In another aspect, the invention provides a compound according to Formula II:

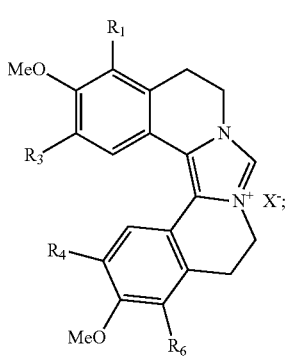

II wherein:

$R_1$, $R_3$, $R_4$, and $R_6$ are each independently H or alkoxy, wherein at least one of $R_1$, $R_3$, $R_4$, and $R_6$ is alkoxy;

$X^-$ is halide, $^-OC(O)$—$R_7$, $^-OSO_2$—$R_7$, or $^-OR_7$; and each $R_7$ is independently H, optionally substituted alkyl, optionally substituted aryl, optionally substituted arylalkyl, haloalkyl, optionally substituted cycloalkyl, optionally substituted heterocycloalkyl, or optionally substituted heteroaryl;

and pharmaceutically acceptable salts, solvates, or hydrates thereof.

Another aspect is a compound of any of the formulae presented herein (e.g., formula I or formula II), wherein $R_2$ and $R_5$ are alkoxy (e.g., methoxy).

Another aspect is a compound of any of the formulae presented herein (e.g., formula I or formula II), wherein at least one of $R_1$, $R_3$, $R_4$, or $R_6$ is alkoxy (e.g., methoxy).

Another aspect is a compound of any of the formulae presented herein (e.g., formula I or formula II), wherein two of $R_1$, $R_3$, $R_4$, or $R_6$ are alkoxy (e.g., methoxy).

Another aspect is a compound of any of the formulae presented herein (e.g., formula I or formula II), wherein $R_3$ and $R_4$ are alkoxy (e.g., methoxy).

Another aspect is a compound of any of the formulae presented herein (e.g., formula I or formula II), wherein $R_1$ and $R_6$ are alkoxy (e.g., methoxy).

Another aspect is a compound of any of the formulae presented herein (e.g., formula I or formula II), wherein each of $R_1$, $R_2$, $R_3$, $R_4$, $R_5$, and $R_6$ is alkoxy (e.g., methoxy).

Another aspect is a compound of any of the formulae presented herein (e.g., formula I or formula II), wherein $X^-$ is halide (e.g., chloride, bromide, fluoride, iodide).

Another aspect is a compound of any of the formulae presented herein (e.g., formula I or formula II), wherein $R_1$ and $R_4$ are H; $R_2$ is alkoxy; and $R_5$ is $C_1$-$C_6$ alkyl or (cycloalkyl)alkyl.

Another aspect is a compound of any of the formulae presented herein (e.g., formula I or formula II), wherein $R_2$ and $R_5$ are alkoxy (e.g., methoxy) and $X^-$ is halide (e.g., chloride, bromide, fluoride, iodide).

Another aspect is a compound selected from the group consisting of:

3,3'-dimethoxy-5,6,8,9-tetrahydro-6a,7a-diazadibenzo[c,g]fluorenium]chloride (1c);

[2,2',3,3'-tetramethoxy-5,6,8,9-tetrahydro-6a,7a-diazadibenzo[c,g]fluorenium]chloride (1a);

3,3',4,4'-tetramethoxy-5,6,8,9-tetrahydro-6a,7a-diazadibenzo[c,g]fluorenium]chloride (1b); and 2,2',3,3',4,4'-hexamethoxy-5,6,8,9-tetrahydro-6a,7a-diazadibenzo[c,g]fluorenium]chloride (1d).

In other aspects, the invention provides a method of treating a disease, disorder, or symptom thereof in a subject, comprising administering to the subject a compound of any of the formulae herein (e.g., formula I or formula II). In another aspect, the compound is administered in an amount and under conditions sufficient to ameliorate the disease, disorder, or symptom thereof in a subject.

In other aspects, the invention provides a method of modulating the proliferation activity in a subject, comprising contacting the subject with a compound of any of the formulae herein (e.g., formula I or formula II), in an amount and under conditions sufficient to modulate proliferation activity.

In other aspects, the invention provides a method of modulating the activity of cell proliferation in a subject, comprising contacting the subject with a compound of any of the formulae herein (e.g., formula I or formula II), in an amount and under conditions sufficient to modulate cell proliferation activity. In another aspect, the cell is a cancer cell. In another aspect, the cell is a tumor cell. In another aspect, the modulation is inhibition.

In one aspect, the invention provides a method of treating a subject suffering from or susceptible to a proliferation related disorder or disease, comprising administering to the subject an effective amount of a compound or pharmaceutical composition of any of the formulae herein (e.g., formula I or formula II).

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, an effective amount of a compound or pharmaceutical composition of any of the formulae herein (e.g., formula I or formula II), such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of any of the formulae herein (e.g., formula I or formula II), such that cell proliferation in said subject is modulated (e.g., down regulated). In another aspect, the compounds delineated herein preferentially target cancer cells over nontransformed cells.

In a specific aspect, the invention provides a method of treating cancer, tumor growth, cancer of the colon, breast, bone, brain and others (e.g., osteosarcoma, neuroblastoma, colon adenocarcinoma), comprising administering to said subject in need thereof, an effective amount of a compound delineated herein (e.g., formula I or formula II), and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

In a specific aspect, the invention provides a method of treating cancer, tumor growth, colon cancer, solid tumor, breast cancer, bone cancer, or brain cancer. In another aspect, the cancer is breast cancer or colon cancer. In another aspect, the breast cancer is hormone refractory. In another aspect, the breast cancer is estrogen receptor (ER), progesterone receptor (PR), and/or human epidermal growth factor receptor 2 (HER2) negative. In another aspect, the breast cancer is triple positive breast cancer. In another aspect, the breast cancer is triple negative breast cancer.

In another aspect, the invention provides a method of inhibiting or blocking mitosis in a cell, comprising contacting said cell with an effective amount of a compound delineated herein (e.g., formula I or formula II), and pharmaceutically acceptable salts thereof. In another aspect, the cell is a cancer cell. In another aspect, the cell is a tumor cell.

In another aspect, the invention provides a method of inhibiting or blocking mitosis in a subject, comprising administering to said subject an effective amount of a compound of a compound delineated herein (e.g., formula I or formula II), and pharmaceutically acceptable salts thereof.

In another aspect, the invention provides a method of treating diseases, disorders, or symptoms thereof mediated by mitosis or apoptosis in a subject in need thereof comprising administering to said subject, an effective amount of a compound delineated herein (e.g., formula I or formula II), and pharmaceutically acceptable salts thereof. In another aspect, the mitosis-mediated disease or disorder is cancer. In another aspect, the cancer is breast cancer or colorectal cancer. In another aspect, the breast cancer is hormone refractory. In another aspect, the breast cancer is estrogen receptor (ER), progesterone receptor (PR), and/or human epidermal growth factor receptor 2 (HER2) negative. In another aspect, the breast cancer is triple negative breast cancer.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.1 mg/kg to about 200 mg/kg, more preferably about 10 mg/kg to about 100 mg/kg of body weight. In other embodiments, the therapeutically effect amount may range from about 1.0 pM to about 500 nM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their minor image partner.

The term "diastereomers" refers to stereoisomers with two or more centers of dissymmetry and whose molecules are not minor images of one another.

The term "enantiomers" refers to two stereoisomers of a compound which are non-superimposable minor images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction)

and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, 2$^{nd}$ Edition, Carlson R, Ed, 2005; Elsevier Science Ltd.; Jahnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

The invention is directed towards macrocyclic compounds, and methods of treating disease and disorders using the compounds or compositions thereof delineated herein.

In other aspects, the invention provides a method of treating a subject suffering from or susceptible to a mitosis related disorder or disease, wherein the subject has been identified as in need of treatment for a mitosis related disorder or disease, comprising administering to said subject in need thereof, an effective amount of a compound or pharmaceutical composition of any of the formulae delineated herein (e.g., formula I or formula II), such that said subject is treated for said disorder. Identifying a subject in need of such treatment can be in the judgment of a subject or a health care professional and can be subjective (e.g. opinion) or objective (e.g. measurable by a test or diagnostic method).

In one aspect, the invention provides a method of modulating the proliferation activity of a cell in a subject, comprising contacting the subject with a compound of any of the formulae delineated herein (e.g., formula I or formula II), in an amount and under conditions sufficient to modulate cell proliferation activity.

In one embodiment, the modulation is inhibition.

In another aspect, the invention provides a method of treating a subject suffering from or susceptible to a cell proliferation related disorder or disease, comprising administering to the subject an effective amount of a compound or pharmaceutical composition of any of the formulae delineated herein (e.g., formula I or formula II).

In other aspects, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or pharmaceutical composition of any of the formulae delineated herein (e.g., formula I or formula II), such that said subject is treated for said disorder.

In certain embodiments, the invention provides a method of treating a disorder, wherein the disorder is cancer (e.g., breast, colon) or solid tumor.

In certain embodiments, the subject is a mammal, preferably a primate or human.

In another embodiment, the invention provides a method as described above, wherein the effective amount of the compound of formula I or formula II ranges from about 0.005 µg/kg to about 200 mg/kg. In certain embodiments, the effective amount of the compound of formula I or formula II ranges from about 0.1 mg/kg to about 200 mg/kg. In a further embodiment, the effective amount of compound of formula I or formula II ranges from about 10 mg/kg to 100 mg/kg.

In other embodiments, the invention provides a method as described above wherein the effective amount of the compound of formula I or formula II ranges from about 1.0 pM to about 500 nM. In certain embodiments, the effective amount ranges from about 10.0 pM to about 1000 pM. In another embodiment, the effective amount ranges from about 1.0 nM to about 10 nM.

In another embodiment, the invention provides a method as described above, wherein the compound of any of the formulae delineated herein (e.g., formula I or formula II) is administered intravenously, intramuscularly, subcutaneously, intracerebroventricularly, orally or topically.

In another embodiment, the invention provides a method as described herein wherein the compound of any of the formulae delineated herein (e.g., formula I or formula II) demonstrates selectivity (e.g., at least 2-fold, at least 5-fold, at least 10-fold, at least X-fold where X is any number between 1 and 20 inclusive) in cell growth activity (e.g., in transformed/nontransformed, MDA-MB-231/NMuMG, U2OS/NIH3T3 cells). In another aspect, the compound of any of the formulae delineated herein (e.g., formula I or formula II) demonstrates selectivity in modulating cell growth activity (e.g., at least 2-fold, at least 5-fold, at least 10-fold, at least X-fold where X is any number between 1 and 20 inclusive) relative to another standard anticancer therapy (e.g., paclitaxel, actinomycin D, doxorubicin).

In other embodiments, the invention provides a method as described above, wherein the compound of any of the formulae delineated herein (e.g., formula I or formula II) is administered alone or in combination with one or more other therapeutics. In a further embodiment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahay, N.J., 1987).

Another object of the present invention is the use of a compound as described herein (e.g., of any formulae herein) in the manufacture of a medicament for use in the treatment of a cell proliferation disorder or disease, or to affect cell differentiation, dedifferentiation or transdifferentiation. Another object of the present invention is the use of a compound as described herein (e.g., of any formulae herein) for use in the treatment of a cell proliferation disorder or disease, or affect cell differentiation, dedifferentiation or transdifferentiation.

Pharmaceutical Compositions

In one aspect, the invention provides a pharmaceutical composition comprising the compound of any of the formulae delineated herein (e.g., formula I or formula II) and a pharmaceutically acceptable carrier.

In another embodiment, the invention provides a pharmaceutical composition further comprising an additional therapeutic agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound of any of the formulae delineated herein (e.g., formula I or formula II), in unit dosage form, together with instructions for administering the compound to a subject suffering from or susceptible to a mitosis mediated disease or disorder.

In one aspect, the invention provides a kit comprising an effective amount of a compound of any of the formulae delineated herein (e.g., formula I or formula II), in unit dosage form, together with instructions for administering the compound to a subject suffering from or susceptible to a cell proliferation disease or disorder, including cancer, solid tumor, angiogenesis, etc.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

General Experimental Parameters

All reactions were conducted in flame-dried glassware under an inert atmosphere of dry argon. THF, $CH_2Cl_2$, and $Et_2O$ were passed through two packed columns of neutral alumina under positive pressure of dry nitrogen prior to use. Toluene was passed through an alumina column and a copper (II) oxide column under positive pressure of dry nitrogen prior to use. All the chemicals used were commercially available and were used as received without further purification. NMR spectra were recorded using a FT-NMR machine, operating at 300 MHz for $^1H$ NMR and at 75.4 MHz for $^{13}C$ NMR. All chemical shifts for $^1H$ and $^{13}C$ NMR spectroscopy were referenced to residual signals from $CDCl_3$ ($^1H$) 7.27 ppm and ($^{13}C$) 77.23 ppm. High resolution mass spectra were recorded on a GC/MS spectrometer or a TOF-LC/MS spectrometer. Compound 6,6',7,7'-tetramethoxy-3,3',4,4'-tetrahydro-1,1'-biisoquinoline was prepared according to the literature. [Judeh, Z. M. A.; Ching, C. B.; Bu, J.; McCluskey, A. Tetrahedron Lett. 2002, 43, 5089]

General Synthetic Methods

Scheme 1 depicts the general synthetic process to prepare the various biisoquinolines. The first step involves the preparation of bis-amides 3a-d by acylation of phenethyl amines 2a-d with diethyl oxalate. The bis-amides 3a-d are then cyclized to afford dihydroisoquinolines 4a-d followed by the treatment with ethyl chloromethyl ether to yield biisoquinolines 1a-d.

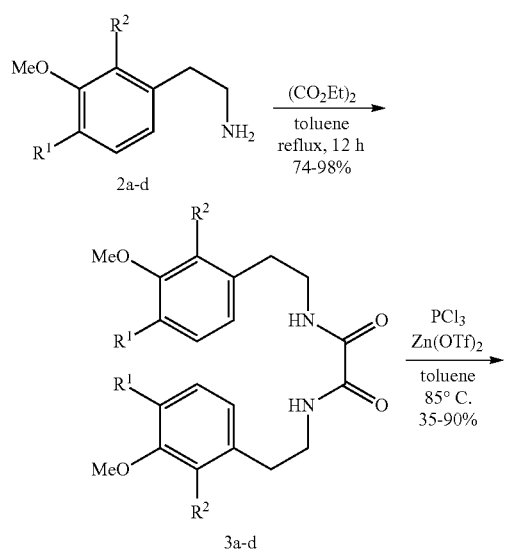

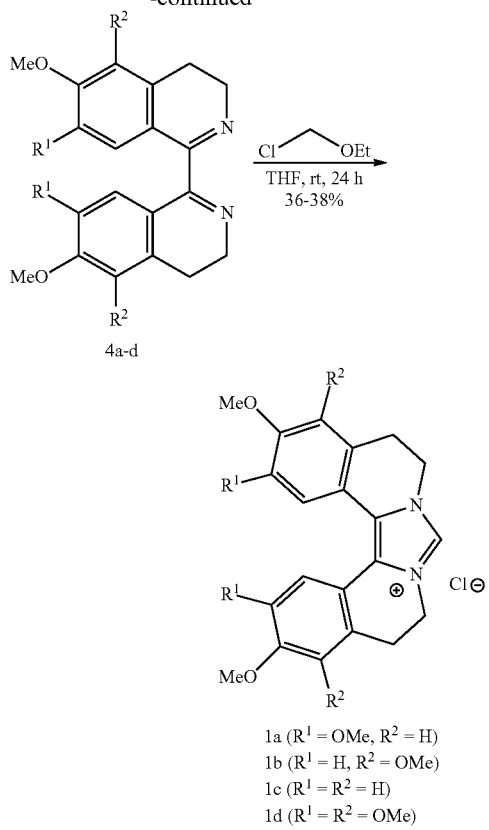

1a ($R^1$ = OMe, $R^2$ = H)
1b ($R^1$ = H, $R^2$ = OMe)
1c ($R^1$ = $R^2$ = H)
1d ($R^1$ = $R^2$ = OMe)

The present invention will now be demonstrated using specific examples that are not to be construed as limiting.

Preparation of Oxalamides 3b-d

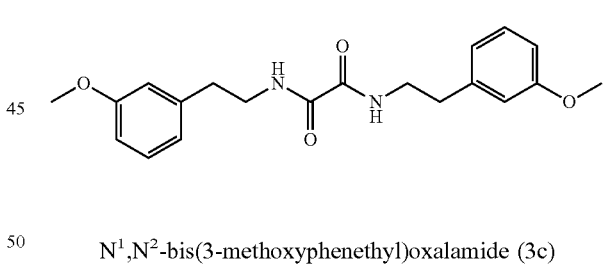

$N^1,N^2$-bis(3-methoxyphenethyl)oxalamide (3c)

To a dry Schlenk flask were added 300 μL (1.917 mmol) of 2-(3-methoxyphenyl)ethanamine, 124 μL (0.913 mmol) of diethyl oxalate and 2 mL of toluene. The reaction mixture was stirred for 12 h at reflux. Then it was cooled to room temperature and hexane (5 mL) was added. The precipitate was filtered and washed with hexane (3×5 mL). Then it was dried under vacuum to yield 325 mg (0.913 mmol, 99%) of N1,N2-bis(3-methoxyphenethyl)oxalamide (3c). $^1H$ NMR (300 MHz, DMSO-$d_6$) δ=8.71 (t, J=5.4 Hz, 1H), 7.19 (t, J=8.2 Hz, 1H), 6.76 (d, J=5.6 Hz, 3H), 3.72 (s, 3H), 3.42-3.34 (m, 2H), 2.76 (t, J=7.2 Hz, 2H). $^{13}C$ NMR (75 MHz, DMSO-$d_6$) δ=159.8, 159.2, 140.6, 129.3, 120.8, 114.1, 111.7, 54.9, 40.1, 34.5. HRMS Calcd. for $C_{20}H_{24}N_2O_4$ [M+Na]$^+$: 379.1628, Found: 379.1620.

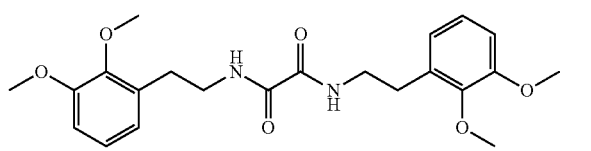

$N^1,N^2$-bis(2,3-dimethoxyphenethyl)oxalamide (3b)

To a dry Schlenk flask were added 300 μL (1.536 mmol) of 2-(2,3-dimethoxyphenyl)ethanamine, 100 μL (0.0.731 mmol) of diethyl oxalate and 2 mL of toluene. The reaction mixture was stirred for 12 h at reflux. Then it was cooled to room temperature and hexane (5 mL) was added. The precipitate was filtered and washed with hexane (3×5 mL). Then it was dried under vacuum to yield 300 mg (0.721 mmol, 99%) of $N^1,N^2$-bis(2,3-dimethoxyphenethyl)oxalamide (3b). $^1$H NMR (300 MHz, DMSO-$d_6$) δ=8.74 (br. s., 1H), 7.06-6.85 (m, 2H), 6.74 (d, J=7.0 Hz, 1H), 3.72 (s, 3H), 3.78 (s, 3H), 3.44-3.33 (m, 2H), 2.89-2.69 (m, 2H). $^{13}$C NMR (75 MHz, DMSO-$d_6$) δ=159.8, 152.3, 146.9, 132.3, 123.7, 121.8, 111.2, 60.1, 55.5, 40.1, 29.0. HRMS Calcd. for $C_{22}H_{28}N_2O_6$ [M+H]$^+$: 417.2020, Found: 417.2002.

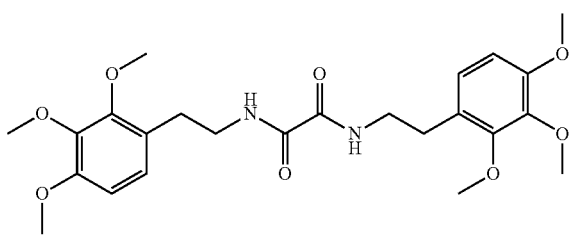

$N^1,N^2$-bis(2,3,4-trimethoxyphenethyl)oxalamide (3d)

To a dry Schlenk flask were added 195 mg (0.923 mmol) of 2-(2,3,4-trimethoxyphenyl)ethanamine, 57 μL (0.419 mmol) of diethyl oxalate and 2 mL of toluene. The reaction mixture was stirred for 12 h at reflux. Then it was cooled to room temperature and hexane (5 mL) was added. The precipitate was filtered and washed with hexane (3×5 mL). Then it was dried under vacuum to yield 90 mg (0.188 mmol, 45%) of $N^1,N^2$-bis(2,3,4-trimethoxyphenethyl)oxalamide (3d). $^1$H NMR (300 MHz, CDCl$_3$) δ=7.63 (t, J=5.1 Hz, 1H), 6.82 (d, J=8.5 Hz, 1H), 6.61 (d, J=8.5 Hz, 1H), 3.91 (s, 3H), 3.87 (s, 3H), 3.85 (s, 3H), 3.54-3.45 (m, 2H), 2.80 (t, J=6.9 Hz, 2H). $^{13}$C NMR (75 MHz, CDCl$_3$) δ=160.0, 153.0, 152.2, 142.5, 124.5, 124.3, 107.5, 61.1, 61.0, 56.2, 40.7, 29.8. HRMS Calcd. for $C_{24}H_{32}N_2O_8$ [M+H]$^+$: 477.2231, Found: 477.2240.

Preparation of bisdihydroisoquinolines 4b-d

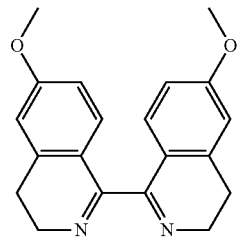 [SMILES: COc1ccc2c(c1)CCN=C2C1=NCCc2cc(OC)ccc21]

6,6'-dimethoxy-3,3',4,4'-tetrahydro-1,1'-biisoquinoline (4c)

To a dry Schlenk flask were added 200 mg (0.561 mmol) of $N^1,N^2$-bis(3-methoxyphenethyl)oxalamide (3c), 610 mg (1.68 mmol) of zinc triflate, 700 mg (3.36 mmol) of phosphorus pentachloride and 28 mL of toluene. The reaction mixture was stirred 6 h at 85° C. Then it was quenched with NH$_4$OH (10 mL) and extracted with ethyl acetate. The organic layer was dried and concentrated under vacuum. The residue was dissolved in dicloromethane (DCM, 20 mL) and extracted with 6 N HCl (3×10 mL). Then the aqueous layer was basified with a solution of 10% wt NaOH and back extracted with DCM. The organic layer was dried with Mg$_2$SO$_4$ and concentrated under vacuum to yield 130 mg (0.406 mmol, 60% yield) of 6,6'-dimethoxy-3,3',4,4'-tetrahydro-1,1'-biisoquinoline (4c). $^1$H NMR (300 MHz, CDCl$_3$) δ=7.21 (d, J=8.5 Hz, 1H), 6.71 (d, J=2.3 Hz, 1H), 6.66 (dd, J=2.6, 8.5 Hz, 1H), 3.93-3.82 (m, 2H), 3.77 (s, 3H), 2.87-2.76 (m, 2H). $^{13}$C NMR (75 MHz, CDCl$_3$) δ=164.7, 161.3, 139.6, 128.7, 121.6, 112.8, 111.7, 55.1, 47.0, 26.3. HRMS Calcd. for $C_{20}H_{20}N_2O_2$ [M+H]$^+$: 321.1598, Found: 321.1597.

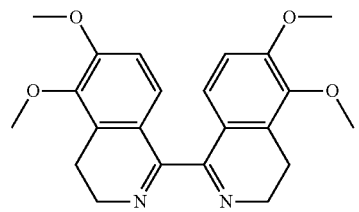

5,5',6,6'-tetramethoxy-3,3',4,4'-tetrahydro-1,1'-biisoquinoline (4b)

44 mg (0.115 mmol, 80% yield) of 5,5',6,6'-tetramethoxy-3,3',4,4'-tetrahydro-1,1'-biisoquinoline (4b) was obtained from 62 mg (0.144 mmol) of $N^1,N^2$-bis(2,3-dimethoxyphenethyl)oxalamide (3b), 180 mg (0.495 mmol) of zinc triflate, 200 mg (0.960 mmol) of phosphorus pentachloride, and 7 mL of toluene. $^1$H NMR (300 MHz, CDCl$_3$) δ=7.08 (br. s., 1H), 6.73 (br. s., 1H), 3.88-3.78 (m, 8H), 2.88 (br. s., 2H). $^{13}$C NMR (75 MHz, CDCl$_3$) δ=165.1, 155.0, 145.3, 131.8, 124.4, 122.5, 109.8, 60.9, 56.0, 47.2, 19.8. HRMS Calcd. for $C_{22}H_{24}N_2O_4$ [M+H]$^+$: 381.1809, Found: 381.1816.

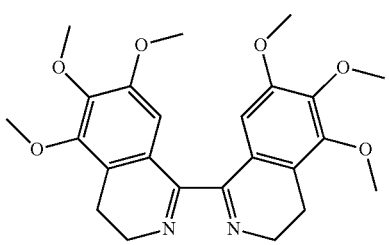

5,5',6,6',7,7'-hexamethoxy-3,3',4,4'-tetrahydro-1,1'-biisoquinoline (4d)

26 mg (0.058 mmol, 35% yield) of 5,5',6,6',7,7'-hexamethoxy-3,3',4,4'-tetrahydro-1,1'-biisoquinoline (4d) was obtained from 80 mg (0.168 mmol) of $N^1,N^2$-bis(2,3,4-trimethoxyphenethyl)oxalamide (3d), 183 mg (0.504 mmol) of zinc triflate, 210 mg (1.008 mmol) of phosphorus pentachloride and 8 mL of toluene. $^1$H NMR (300 MHz, CDCl$_3$) δ=6.74 (s, 1H), 3.96-3.82 (m, 9H), 3.74 (s, 3H), 2.79 (t, J=7.6 Hz, 2H). $^{13}$C NMR (75 MHz, CDCl$_3$) δ =164.5, 151.7, 149.9, 144.9, 124.5, 123.7, 107.3, 61.0, 60.9, 56.1, 47.1, 18.9. HRMS Calcd. for $C_{24}H_{28}N_2O_6$ [M+H]$^+$: 441.2020, Found: 441.2025.

Preparation of bisdihydroisoquinolines 1a-d

Example 1

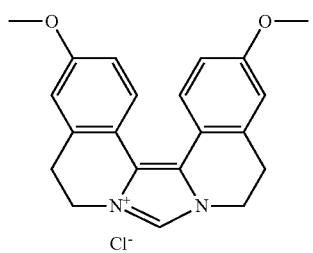

3,3'-dimethoxy-5,6,8,9-tetrahydro-6a,7a-diazadibenzo[c,g]fluorenium]chloride (1c)

To a solution of 6,6',7,7'-tetramethoxy-3,3',4,4'-tetrahydro-1,1'-bisisoquinoline (4c) 0.049 g (0.129 mmol) in THF (3 mL) was added chloromethyl ethyl ether 73 μL (0.786 mmol). The reaction mixture was stirred for 12 h. Volatiles were removed in vacuo and the resulting sticky residue was purified by flash column chromatography (silica gel, 10:1 CH$_2$Cl$_2$/MeOH) to yield 0.020 g (0.047 mmol, 36.4%) of 2,2',3,3'-tetramethoxy-5,6,8,9-tetrahydro-6a,7adiazadibenzo[c,g]fluorenium]chloride (1c). $^1$H NMR (299 MHz, CDCl$_3$) δ=10.61 (br. s., 1H), 7.83 (d, J=8.2 Hz, 2H), 6.91-6.82 (m, 4H), 4.51 (br. s., 4H), 3.86 (s, 6H), 3.13 (br. s., 4H). $^{13}$C NMR (75 MHz, CDCl$_3$) δ=160.7, 135.6, 125.8, 123.7, 116.4, 114.3, 113.5, 55.5, 43.9, 29.2. HRMS Calcd. for $C_{21}H_{21}ClN_2O_2$ [M+H]$^+$: 333.1598, Found: 333.1593.

Example 2

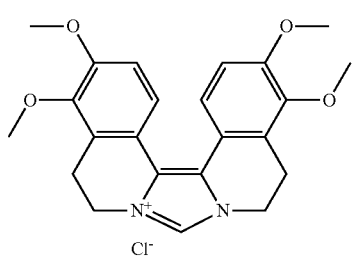

3,3',4,4'-tetramethoxy-5,6,8,9-tetrahydro-6a,7a-diazadibenzo[c,g]fluorenium]chloride (1b)

To a solution of 6,6',7,7'-tetramethoxy-3,3',4,4'-tetrahydro-1,1'-bisisoquinoline (4b) 0.049 g (0.129 mmol) in THF (3 mL) was added chloromethyl ethyl ether 73 μL (0.786 mmol). The reaction mixture was stirred for 12 h. Volatiles were removed in vacuo and the resulting sticky residue was purified by flash column chromatography (silica gel, 10:1 CH$_2$Cl$_2$/MeOH) to yield 0.020 g (0.047 mmol, 36.4%) of 2,2',3,3'-tetramethoxy-5,6,8,9-tetrahydro-6a,7adiazadibenzo[c,g]fluorenium]chloride (1b). $^1$H NMR (300 MHz, CDCl$_3$) δ=10.44 (br. s., 1H), 7.69 (d, J=8.5 Hz, 2H), 6.88 (d, J=8.8 Hz, 1H), 4.47 (t, J=6.2 Hz, 4H), 3.93 (s, 6H), 3.87 (s, 6H), 3.22 (t, J=6.2 Hz, 4H). $^{13}$C NMR (75 MHz, CDCl$_3$) δ=153.9, 146.4, 134.1, 128.1, 123.8, 120.5, 117.0, 111.0, 61.0, 55.9, 43.8, 22.0. HRMS Calcd. for $C_{23}H_{25}ClN_2O_4$ [M]$^+$: 393.1809, Found: 393.1822.

Example 3

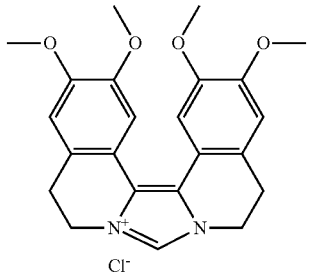

2,2',3,3'-tetramethoxy-5,6,8,9-tetrahydro-6a,7a-diazadibenzo[c,g]fluorenium]chloride (1a)

To a solution of 6,6',7,7'-tetramethoxy-3,3',4,4'-tetrahydro-1,1'-bisisoquinoline (4b) 0.049 g (0.129 mmol) in THF (3 mL) was added chloromethyl ethyl ether 73 μL (0.786 mmol). The reaction mixture was stirred for 12 h. Volatiles were removed in vacuo and the resulting sticky residue was purified by flash column chromatography (silica gel, 10:1 CH$_2$Cl$_2$/MeOH) to yield 0.020 g (0.047 mmol, 36.4%) of 2,2',3,3'-tetramethoxy-5,6,8,9-tetrahydro-6a,7adiazadibenzo[c,g]fluorenium]chloride (1b). $^1$H NMR (300 MHz, CDCl$_3$) δ=10.44 (br. s., 1H), 7.69 (d, J=8.5 Hz, 2H), 6.88 (d, J=8.8 Hz, 1H), 4.47 (t, J=6.2 Hz, 4H), 3.93 (s, 6H), 3.87 (s, 6H), 3.22 (t, J=6.2 Hz, 4H). $^{13}$C NMR (75 MHz, CDCl$_3$) δ=153.9, 146.4, 134.1, 128.1, 123.8, 120.5, 117.0, 111.0, 61.0, 55.9, 43.8, 22.0. HRMS Calcd. for $C_{23}H_{25}ClN_2O_4$ [M]$^+$: 393.1809, Found: 393.1822.

Example 4

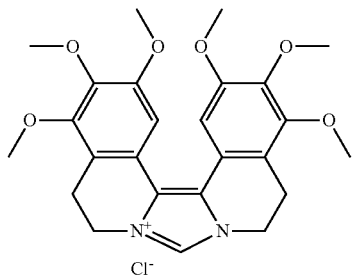

2,2',3,3',4,4'-hexamethoxy-5,6,8,9-tetrahydro-6a,7a-diazadibenzo[c,g]fluorenium]chloride (1d)

To a solution of 5,5',6,6',7,7'-hexamethoxy-3,3',4,4'-tetrahydro-1,1'-biisoquinoline (4d) (0.049 g, 0.129 mmol) in THF (3 mL) was added chloromethyl ethyl ether (73 μL, 0.786 mmol). The reaction mixture was stirred for 12 h. Volatiles were removed in vacuo and the resulting sticky residue was purified by flash column chromatography (silica gel, 10:1 $CH_2Cl_2$/MeOH) to yield 0.020 g (0.047 mmol, 36.4%) of 2,2',3,3',4,4'-hexamethoxy-5,6,8,9-tetrahydro-6a,7adiazadibenzo[c,g]fluoreniuml chloride (1d). $^1$H NMR (299 MHz, CDCl$_3$) δ=10.74 (br. s., 1H), 7.24 (s, 2H), 4.49 (br. s., 4H), 3.94 (s, 6H), 3.93 (s, 6H), 3.76 (s, 6H), 3.16 (br. s., 4H). $^{13}$C NMR (75 MHz, CDCl$_3$) δ=152.8, 151.4, 144.0, 124.1, 121.2, 119.0, 104.4, 61.2, 61.1, 56.5, 44.2, 29.7. HRMS Calcd. for $C_{25}H_{29}ClN_2O_6$ [M]$^+$: 453.2020, Found: 453.1999.

Example 5: Maintenance of Mammalian Cell Lines

The following human breast cancer cell lines were used in these studies: (a) Triple-positive: BT474, MCF7 and T47D, (b) Triple-negative: MDA-MB231 and MDA-MB468. Cells were grown in the following medium at 37° C. under a humidified atmosphere of 5% $CO_2$: DMEM (BT474 cells), RPMI (MCF7 and T47D cells) and MEM (MDA-MB231 and MDA-MB468 cells). For each cell line, the medium was supplemented with 10% fetal bovine serum (Hyclone, Logan, Utah) 100 U/ml of penicillin, and 100 μg/ml of streptomycin.

Example 6: Cell Growth Inhibition Assay

Cells were trypsinized and a single cell suspension was prepared. Cells were plated at a density of $5\times10^2$-$1\times10^3$ cells in 60 mm tissue culture plates. After the attachment, cells were treated with different concentrations of biisoquinolines 1a-d for 48 h. After the treatment, medium containing drug was removed and supplemented with fresh medium. Cells were allowed to grow into colonies for additional 10 days. Colonies were fixed, stained with 0.3% (w/v) methylene blue, and excess of the dye was removed after washing with PBS. Colonies containing more than fifty cells were counted and the IC$_{50}$ values, i.e., drug concentrations required for 50% growth inhibition of these cell lines were determined as described in our previous studies. [Balusu, R.; Jaiswal, A. S.; Armas, M. L.; Kundu, C. N.; Bloom L, B.; Narayan S. *Biochemistry* 2007, 46, 13961; Jaiswal, A, S.; Banerjee, S.; Panda, H.; Bulkini, C. D.; Izumi, T.; Sarkar, F. H.; Ostrov, D. A.; Narayan, S. *Mol. Cancer Res.* 2009, 7, 1973] The IC$_{50}$ of each compound was determined from the survival curve using the SigmaPlot-10.0 software program.

Example 7: MDA-MB231 Growth Inhibition 6,6',7,7'-tetramethoxy biisoquinoline-imidazolium 1a, as well as its precursor compounds, bisamide 3a, and diimine 4a, were tested for the growth inhibitory effect on MDA-MB-231 cells by using the clonogenic cell survival assay [Balusu, R.; Jaiswal, A. S.; Armas, M. L.; Kundu, C. N.; Bloom L, B.; Narayan S. *Biochemistry* 2007, 46, 13961; Jaiswal, A, S.; Banerjee, S.; Panda, H.; Bulkin, C. D.; Izumi, T.; Sarkar, F. H.; Ostrov, D. A.; Narayan, S. *Mol. Cancer Res.* 2009, 7, 1973]. Imidazolium 1a displayed a notable cytotoxicity (IC$_{50}$=19 μM), whereas bisamide 3a showed less potency (IC$_{50}$=45 μM) and diimine 4a was non-toxic to the MDA-MB231 cells. These initial results seem to suggest that the structural rigidity might be important for the antitumor activity. Then, three other methoxylated biisoquinoline-imidazolium compounds (1b-d) were tested to probe the optimal methoxy substitution pattern. 6,6'-dimethoxy compound 1c displayed the lowest IC$_{50}$ value of 4.7 μM among the four compounds tested. Tetramethoxy compounds 1a and 1b showed higher IC$_{50}$ values (19 μM and 18.2 μM respectively), and hexamethoxy compound 1d did not show any toxicity to the MDA-MB231 cells.

Example 8: Growth Inhibition in Triple-Positive Breast Cancer Cell Lines

The anti-cancer therapeutic efficacy of the biisoquinoline compounds was evaluated for triple-positive (BT474, MCF7 and T47D) breast cancer cell lines. The IC$_{50}$ values of 6,6',7,7'-tetramethoxy biisoquinoline-imidazolium 1a for BT474, MCF7 and T47D cell lines were 3.1 μM, 35 μM and 34 μM, respectively, suggesting that BT474 cells were more sensitive to 1a than MCF7 or T47D cells. Further analysis showed that 5,5',6,6'-tetramethoxy bisamide 3b was sensitive to only BT474 cells (IC$_{50}$=34.1 μM), while MCF7 and T47D were resistant to this molecule. The IC$_{50}$ values of 5,5',6,6'-tetramethoxy imidazolium 1b were 0.7 μM, 7.9 μM, and 13.5 μM for BT474, MCF7, and T47D cell lines, respectively, while those of 6,6'-dimethoxy imidazolium 1c were 0.3 μM, 1.3 μM, and 1.0 μM, respectively. Thus, two compounds, 1b and 1c have potent growth inhibitory effect on triple-positive breast cancer cells and the more potent compound appears to be 1c.

Example 9: Growth Inhibition in Triple-Negative Breast Cancer Cell Lines

The anti-cancer therapeutic efficacy of the biisoquinoline compounds was evaluated for triple-negative (MDA-MB231 and MDAMB468) breast cancer cell lines. The IC$_{50}$ values of 6,6',7,7'-tetramethoxy imidazolium 1a were 20.8 μM and 2.6 μM for MDA-MB231 and MDA-MB468 cell lines, respectively. On the other hand, the IC$_{50}$ value of 5,5',6,6'-tetramethoxybisamide 3b was 35.4 μM for MDA-MB468 cells, while it did not show any cytotoxicity on MDA-MB231 cells. The IC$_{50}$ values of 5,5',6,6'-tetramethoxy imidazolium 1b were 14.2 μM and 2.1 μM for MDA-MB231 and MDA-MB468 cell lines, respectively, while those of 6,6'-dimethoxy imidazolium 1c were 2.4 μM and 1.8 µM. These results indicate the successful identification of a potential anti-cancer drug candidate 1c, which sensitizes both triple-positive and triple-negative breast cancer cell lines at low µM level concentrations. The current result could be significant as overall survival of patients with triple-negative breast cancer is poor compared to other phenotypes. The triple-negative breast cancer lacks the expression of ER, PR and HER2 expression; therefore, their clinical management is very difficult. Triple-negative breast cancer is not suitable for hormonal- or HER2-dire cted therapy [Bauer K. R.; Brown, M.; Cress, R. D.; Parise, C. A.; Caggiano, V. *Cancer* 2007, 109, 1721; Rakha, E. A.; El-Sayed, M. E.; Green, A. R.; Lee, A. H.; Robertson, J. F.; Ellis, I. O. *Cancer* 2007, 109, 25; Dent, R.; Trudeau, M.; Pritchard, K. I.; Hanna, W. M.; Kahn, H. K.; Sawka, C. A.; Lickley, L. A.; Rawlinson, E.; Sun, P.; Narod, S. A. *Clin. Cancer Res.* 2007, 13, 4429]. While a number of targeted therapies, such as poly(ADP-ribose)polymerase inhibitors, are recently undergoing for clinical evaluations [Pal, S. K.; Childs, B. H.; Pegram, M. *Breast Cancer Res. Treat.* 2011, 125, 627; Leung, M.; Rosen, D.; Fields, S.; Cesano, A.; Budman, D. R. *Mol. Med.* 2011, 17, 854; Liu, J. F.; Tolaney, S. M.; Birrer, M.; Fleming, G. F.; Buss, M. K.; Dahlberg, S. E.; Lee, H.; Whalen, C.; Tyburski, K.; Winer, E.; Ivy, P.; Matulonis, U. A. *Eur. J. Cancer,* 2013, 49, 2972; Sandhu, S. K.; Schelman, W. R.; Wilding, G.; Moreno, V.; Baird, R. D.; Miranda, S.; Hylands, L.; Riisnaes, R.; Forster, M.; Omlin, A.; Kreischer, N.; Thway, K.; Gevensleben, H.; Sun, L.; Loughney, J.; Chatterjee, M.; Toniatti, C.; Carpenter, C. L.; Iannone, R.; Kaye, S. B.; de Bono, J. S.; Wenham, R. M. *Lancet Oncol.* 2013, 14, 882], the current result might offer another potential strategy to deal with the triple-negative breast cancer.

Example 10: Comparison to Noscapine

Noscapine was used as a reference compound to assess the efficacy of compound 1c as a therapeutic for triple-positive and triple-negative breast cancer. When both compounds were assessed using protocols essentially as described herein, results showed that noscapine has $IC_{50}$ values of 57 µM and 64 µM for MCF7 and MDA-MB-231 cell lines, respectively, which are 44- and 16-folds higher than the $IC_{50}$ values for compound 1c for these cell lines.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed is:

1. A compound according to Formula I:

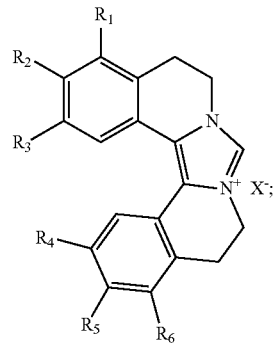

wherein:
$R_1$, $R_2$, $R_3$, $R_4$, $R_5$, and $R_6$ are each independently H or alkoxy;
$X^-$ is halide, $^-OC(O)-R_7$, $^-OSO_2-R_7$, or $^-OR_7$; and
each $R_7$ is independently H, optionally substituted alkyl, optionally substituted aryl, optionally substituted arylalkyl, haloalkyl, optionally substituted cycloalkyl, optionally substituted heterocycloalkyl, or optionally substituted heteroaryl;
wherein at least one of $R_1$, $R_3$, $R_4$, or $R_6$ is alkoxy.

2. A compound according to Formula II:

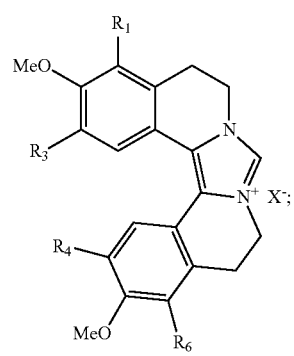

wherein:
$R_1$, $R_3$, $R_4$, and $R_6$ are each independently H or alkoxy;
$X^-$ is halide, $^-OC(O)-R_7$, $^-OSO_2-R_7$, or $^-OR_7$; and
each $R_7$ is independently H, optionally substituted alkyl, optionally substituted aryl, optionally substituted arylalkyl, haloalkyl, optionally substituted cycloalkyl, optionally substituted heterocycloalkyl, or optionally substituted heteroaryl.

3. The compound of claim 2, wherein one of $R_1$, $R_3$, $R_4$, or $R_6$ is alkoxy.

4. The compound of claim 2, wherein two of $R_1$, $R_3$, $R_4$, or $R_6$ are alkoxy.

5. The compound of claim 4, wherein $R_3$ and $R_4$ are alkoxy.

6. The compound of claim 5, wherein $R_3$ and $R_4$ are methoxy.

7. The compound of claim 4, wherein $R_1$ and $R_6$ are alkoxy.

8. The compound of claim 7, wherein $R_1$ and $R_6$ are methoxy.

9. The compound of claim 2, wherein each of $R_1$, $R_3$, $R_4$, and $R_6$ is alkoxy.

10. The compound of claim 9, wherein each of $R_1$, $R_3$, $R_4$, and $R_6$ is methoxy.

11. The compound of claim 2, wherein $X^-$ is halide.

12. The compound of claim 11, wherein $X^-$ is chloride.

13. The compound of claim 2, wherein the compound is selected from the group consisting of:
   3,3'-dimethoxy-5,6,8,9-tetrahydro-6a,7a-diazadibenzo[c,g]fluorenium]chloride (1c);
   [2,2',3,3'-tetramethoxy-5,6,8,9-tetrahydro-6a,7a-diazadibenzo[c,g]fluorenium]chloride (1a);
   3,3',4,4'-tetramethoxy-5,6,8,9-tetrahydro-6a,7a-diazadibenzo[c,g]fluorenium]chloride (1b); and
   2,2',3,3',4,4'-hexamethoxy-5,6,8,9-tetrahydro-6a,7a-diazadibenzo[c,g]fluorenium]chloride (1d).

14. A method of treating a subject suffering from or susceptible to breast cancer, comprising administering to said subject, an effective amount of a compound of claim 2.

15. The method of claim 14, wherein the breast cancer is hormone refractory.

16. The method of claim 14, wherein the breast cancer is triple-positive breast cancer.

17. The method of claim 14, wherein the breast cancer is estrogen receptor (ER), progesterone receptor (PR, and/or human epidermal growth factor receptor 2 (HER2) negative.

18. The method of claim 17, wherein the breast cancer is triple negative breast cancer.

19. A pharmaceutical composition comprising a compound of claim 2.

* * * * *